[19] United States Patent
Heinecke

[11] Patent Number: 5,088,483
[45] Date of Patent: Feb. 18, 1992

[54] ADHESIVE FRAME BANDAGE

[75] Inventor: Steven B. Heinecke, New Richmond, Wis.

[73] Assignee: Minnesota Mining and Manufacturing Co., St. Paul, Minn.

[21] Appl. No.: 672,777

[22] Filed: Mar. 20, 1991

Related U.S. Application Data

[63] Continuation of Ser. No. 267,230, Nov. 4, 1988, abandoned.

[51] Int. Cl.⁵ .................... A61F 13/00; A61F 19/00
[52] U.S. Cl. ...................... 602/46; 128/849; 206/441; 206/447; 602/52; 602/57
[58] Field of Search .............. 128/155, 156, 849, 850, 128/851, 852; 604/304, 307, 366, 389; 206/440, 441, 447

[56] References Cited

U.S. PATENT DOCUMENTS

| | | |
|---|---|---|
| 1,707,515 | 4/1929 | Evans . |
| 3,062,683 | 11/1962 | Kalleberg et al. . |
| 3,260,260 | 7/1966 | Questel . |
| 3,349,765 | 10/1967 | Blanford . |
| 3,364,928 | 1/1968 | Creager, Jr. et al. . |
| 3,452,750 | 7/1969 | Blanford . |
| 3,645,835 | 2/1972 | Hodgson . |
| 3,885,559 | 5/1975 | Economou ..................... 128/156 |
| 3,916,887 | 11/1975 | Kelly . |
| 4,253,460 | 3/1981 | Chen et al. ................. 128/156 X |
| 4,302,500 | 11/1981 | Flora ............................... 428/284 |
| 4,372,303 | 2/1983 | Grossmann et al. . |
| 4,374,520 | 2/1983 | Grossmann et al. . |
| 4,394,904 | 7/1983 | Larimore . |
| 4,485,809 | 12/1984 | Dellas . |
| 4,499,896 | 2/1985 | Heinecke . |
| 4,513,739 | 4/1985 | Johns . |
| 4,545,371 | 10/1985 | Grossmann et al. . |
| 4,595,001 | 6/1986 | Potter et al. . |
| 4,600,001 | 7/1986 | Gilman . |
| 4,614,183 | 9/1986 | McCracken et al. . |
| 4,678,462 | 7/1987 | Vaillencourt . |
| 4,706,662 | 11/1987 | Thompson . |
| 4,734,320 | 3/1988 | Ohira et al. ................. 128/156 X |
| 4,744,355 | 5/1988 | Faasse, Jr. ..................... 128/156 |
| 4,753,232 | 6/1988 | Ward . |
| 4,832,008 | 5/1989 | Gilman ....................... 128/156 X |
| 4,917,112 | 4/1990 | Kalt ............................... 128/156 |

FOREIGN PATENT DOCUMENTS 0051935 5/1982 European Pat. Off. .
842617 7/1960 United Kingdom .

OTHER PUBLICATIONS

Veni-Gard Brochure (N83-20M).
Veni-Gard AP/TPN Brochure (JA 84-20M).

Primary Examiner—Randall L. Green
Assistant Examiner—Paul Prebilic
Attorney, Agent, or Firm—Gary L. Griswold; Walter N. Kirn; Dale A. Bjorkman

[57] ABSTRACT

An adhesive composite is provided which consists of a conformable backing, a pressure-sensitive adhesive which is coated on at least a portion of the bottom surface of the backing, a permanent adhesive reinforcement which acts as reinforcing means for the backing, coated on the bottom surface of the film and a liner which is releasably applied to the adhesive coated surface of the backing. A delivery means may also be provided to allow delivery of the system without touching the adhesive. The permanent adhesive reinforcement is applied to the backing in an amount which is sufficient to provide some reinforcement to the thin film backing so that the composite wall not tend to fold back on itself or wrinkle under ordinary use. Preferably this permanent adhesive reinforcement is applied to the periphery of the backing.

23 Claims, 2 Drawing Sheets

ADHESIVE FRAME BANDAGE

This is a continuation of Application No. 07/267,230 filed Nov. 4, 1988 now abandoned.

Field of Invention

The present invention relates to pressure-sensitive adhesive composites comprising a backing coated on one side with adhesive. More particularly, it relates to pressure-sensitive adhesive composites having improved means for handling and application to a surface. The invention is of particular benefit in the application of backings which are very thin, adhesive-coated transparent films widely used as medical dressings.

BACKGROUND

Although the present invention is useful in any adhesive composite needing a delivery system, it has particular benefit in connection with transparent film dressings and surgical drapes. These dressings and drapes are widely used as a protective layer over a wound, facilitating healing in a moist environment while acting as a barrier to liquids and bacteria. Dressings of this type are available under trade names such as Tegaderm TM (3M, St. Paul, Minn.), Bioclusive TM (Johnson & Johnson, New Brunswick, N.J.), Op-Site TM (T. J. Smith & Nephew, Hull, England) and Uniflex TM (Howmedica, Largo, Fla.).

The polymeric films used in such dressings are conformable. By this it is meant that these films are extremely thin, flimsy, and supple. They are supplied with a releasable protective liner overlying the adhesive coated surface of the film. When the liner is removed, the adhesive coated film tends to wrinkle and stick to itself interfering with the smooth aseptic application of the dressing or drape to the skin. Various delivery systems have been proposed to obviate this problem.

One such delivery system utilizes a removable frame to support the edges of the film during its application. U.S. Pat. No. 4,372,303 describes a composite having a relatively thin polymeric film which is conformable to animal anatomic surfaces. A pressure-sensitive adhesive is coated on one surface of the polymeric film, a release liner is attached to the adhesive coated surface of the film, and a frame is attached to the exposed surface of the film. In use the frame stays with the film until the film is affixed to the skin, at which time it is removed.

Another delivery system is described in U.S. Pat. No. 4,513,739. That patent describes a wound dressing comprising a film that is coated on one face with a biocompatible adhesive. One or more liner sheets are releasably adhered to the adhesive coated surface. Release retarding means are provided along one edge or a pair of opposed edges of the dressing to require a greater force to separate the layers (film, adhesive, and liner) at the edge or edges than at the remainder of the contact area. The release retarding means may be a thicker strip of the polymeric film, a stiffer piece of film adhered to the film at its edges, a strip of liner wrapped around the edge of the film and adhered to the exposed surface of the film, or a strip attached to the exposed surfaces of both the film and the liner. Alternatively, a more aggressive adhesive may be used at the edges than on the central portion of the dressing.

A third delivery system is described in U.S. Pat. No. 4,485,809. In this system, a window frame of liner material is provided for support during placement of the dressing by removal of a center section of the release liner. The window frame is then removed by separation of the film at the perforations provided within the area of the frame.

A fourth delivery system is used in the Veni-gard ® dressing (Conmed, Utica, N.Y.). In this dressing, a permanently attached foam frame is provided on the non-adhesive side of the film backing.

An additional problem which occurs in the use of thin film adhesive dressings is the premature release of the dressing from the skin, generally initiated by failure of the adhesive at the edges of the dressing. Practitioners will occasionally secure the edges of the dressing with medical tape in order to avoid this problem. This is a very inefficient solution to the "edge lift" problem involving additional materials and time.

SUMMARY OF THE INVENTION

The adhesive composite of this invention contains a conformable backing (having top and bottom faces), a pressure-sensitive adhesive coated on at least a portion of the bottom face of the backing (hereinafter backing adhesive), a permanent adhesive reinforcement on the bottom face of the backing which acts as reinforcing means for the backing, and a liner releasably applied to the adhesive coated face of the backing. The permanent adhesive reinforcement can additionally enhance adhesion of the composite to a surface. Preferably, delivery means are provided to allow application of the system without touching the adhesive.

The backing is preferably a polymeric film which is impermeable to liquid water but is permeable to moisture vapor and is coated with adhesive on the bottom face. When a high moisture vapor permeable film is used, the adhesives are preferably biocompatible. Most preferably the film/adhesive composite is transparent and comprises a high moisture vapor permeable film and a high moisture vapor permeable biocompatible adhesive.

The permanent adhesive reinforcement is present in an amount which is sufficient to provide some reinforcement to the conformable backing so that the composite will tend not to fold back on itself or wrinkle during application to a surface. This permanent adhesive reinforcement may be a laminate of an adhesive and a substrate such as a film or fabric. Alternatively, the reinforcement properties of the permanent adhesive reinforcement may be provided by bulk of the adhesive itself or the addition of fibers or other reinforcing materials to the adhesive. When the permanent adhesive reinforcement is an adhesive laminate that is affixed to the backing after the bottom face of the backing is coated with a pressure-sensitive adhesive, it is affixed with the adhesive face exposed so that the permanent adhesive reinforcement will adhere to the skin or other surface to which the composite is applied. The permanent adhesive reinforcement may be provided on the backing in any pattern which will reinforce and improve the handleability of the backing. For example, the reinforcement may be provided in strips along at least the two opposed edges of the backing which bridge the edges held by the user during application. Preferably, the permanent adhesive reinforcement is applied to the periphery of the backing on the bottom face of the backing after the backing has been coated with the pressure-sensitive adhesive.

In addition to reinforcing the flimsy backing, the permanent adhesive reinforcement also can provide a better edge seal of the composite to the surface to which it is applied by providing a higher tack adhesive along the edges of the composite. The permanent adhesive reinforcement can flex in response to movement of the underlying surface, thereby not detracting from the conformability and comfort of the composite. This is especially desirable when the composite is used as a medical dressing. Also, because the permanent adhesive reinforcement is comparatively thin and is located on the adhesive coated face of the backing, the composite as a whole presents a very low profile. A medical dressing of this invention does not present a high profile of reinforcing material which could catch on bedsheets, etc.

The liner may be comprised of any conventional liner material. For example, the liner could be paper which preferably has been coated with a release agent, such as silicone.

The delivery means may be any method of providing application of the composite to a surface. Such means may be separate tabs removably or permanently bonded to the backing on the non-adhesive coated face, or may be appropriate die cuts of the liner which allow for the separate removal of portions of the liner from the adhesive-coated backing. Thus, the delivery means may or may not be a separately identifiable physical structure of the adhesive composite.

DESCRIPTION OF DRAWINGS

Figure 1:
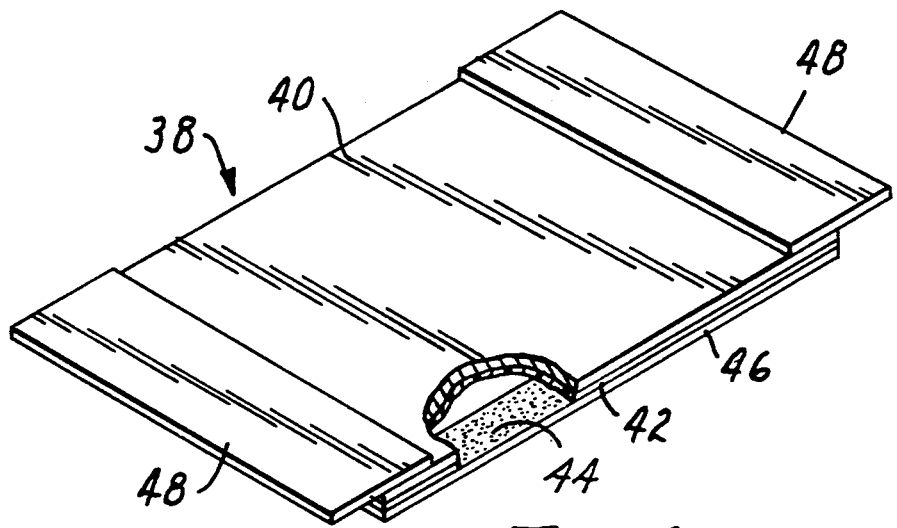
FIG. 1 is a perspective view of a film dressing according to the present invention with parts cut away.

FIG. 1 shows a dressing embodiment 38 of the present invention. The backing 40 is made of a thin transparent, polymeric film which is moisture vapor permeable and liquid and bacteria impermeable such as a polyester or polyurethane film. Backing adhesive 42 is an adhesive exhibiting low irritation to skin, preferably a hypoallergenic acrylate copolymer bioadhesive. Backing adhesive 42 covers at least a portion of backing 40 and here is illustrated to cover the entire bottom face of the film. A reinforcing amount of a permanent adhesive reinforcement 44 in the form of an adhesive or an adhesive laminate is applied to at least a portion of backing 40 on the same side of backing 40 as backing adhesive 42. A liner 46 covers the adhesives. Liner 46 is optionally die cut or may optionally extend beyond the adhesive coated face of backing 40 to enable easy removal by the user. Tabs 48 are affixed to the non-adhesive coated face of backing 40 for ease in handling and application of dressing 38 to a surface such as skin without the need to contact backing adhesive 42 with the fingers. Tabs 48 may be permanently affixed to backing 40 by heat-sealing or with an adhesive, or may be removably affixed to backing 40 by light heat-sealing, by a physical clamping mechanism such as disclosed in U.S. Pat. No. 4,374,520, or by a releasable amount of an adhesive. In application, the user holds dressing 38 by one of tabs 48 while removing liner 46 with the other hand. The other tab 48 is then grasped by the free hand and dressing 38 is applied to the skin. Finally, tabs 48 are removed if this option is provided.

FIGS. 2-5 show a preferred dressing embodiment 8 of the present invention. In this embodiment the liner has been die out with two parallel cuts 20 to create a middle portion 22 and end portions 24. Of course, any arrangement of die cuts on the liner that allows selective removal of portions of the liner are contemplated as alternative embodiments of this delivery system. Middle portion 22 is first removed and dressing 8 is applied to the skin.

Figure 2:
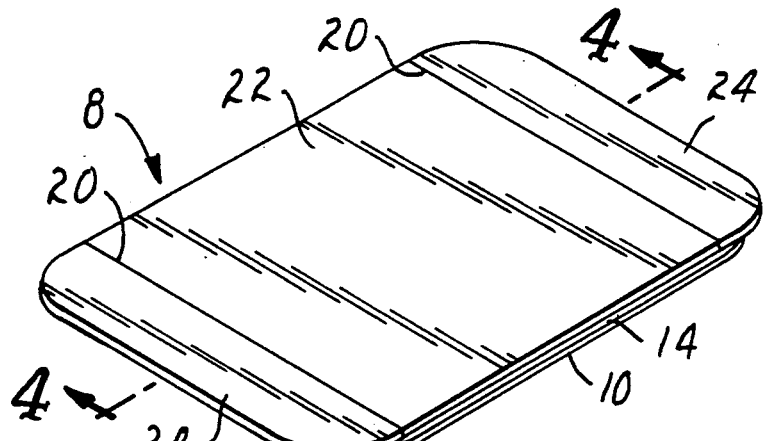
FIG. 2 is a perspective view of an alternative embodiment of a film dressing of this invention.
Figure 3:
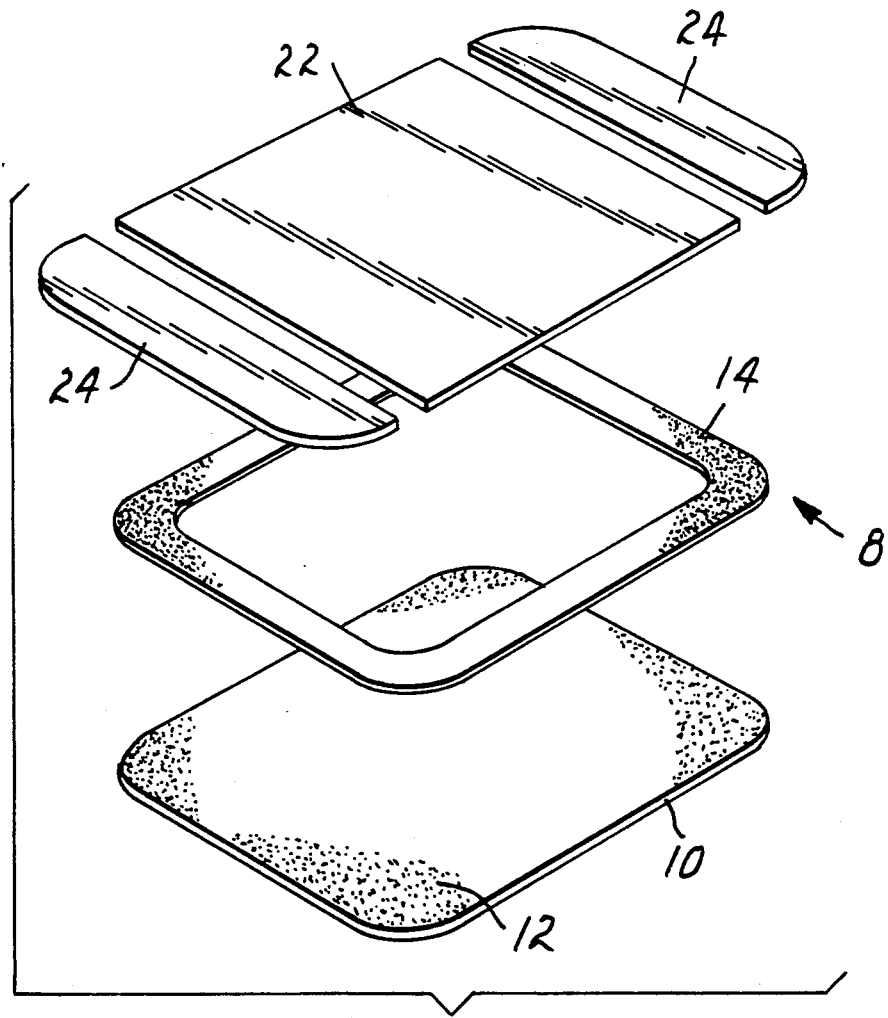
FIG. 3 is an exploded view of the film dressing of FIG. 2.

FIG. 3 shows an exploded view of the dressing of FIG. 2 providing the relative positioning of backing 10, backing adhesive 12 coated on one face of backing 10, and the peripheral frame of permanent adhesive reinforcement 14 between backing adhesive 12 and liner portions 22 and 24, with its sticky surface exposed upon removal of liner portions 22 and 24. In a less preferred alternative embodiment, backing adhesive 12 and permanent adhesive reinforcement 14 may be interchanged with respect to their relative position on backing 10. Permanent adhesive reinforcement 14 in such an embodiment still provides improved handling properties, but when permanent adhesive reinforcement 14 is not exposed to the skin, the advantages of using a higher tack adhesive in permanent adhesive reinforcement 14 are not available.

An alternative three part liner embodiment would provide J-folds for ease in separation as disclosed in U.S. Pat. No. 4,614,183.

Figure 4:
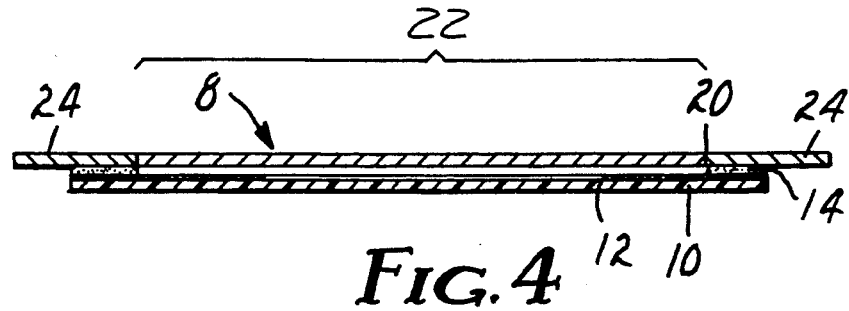
FIG. 4 is a cross-sectional view of the film dressing of FIG. 2 taken along line 4—4.

FIG. 4 shows a cross-sectional view of the dressing of FIG. 2 taken along the line 4—4. In applying dressing 8 to the skin, the user may avoid contact with backing adhesive 12 and permanent adhesive reinforcement 14 by grasping liner edge portions 24. Liner middle portion 22 is removed from backing 10 by bending dressing 8 in such a manner that liner middle portion 22 begins to separate from backing adhesive 12, providing a free area to grasp to facilitate complete removal of middle portion 22. The corresponding adhesive coated face of backing 10 is pressed to the skin. Liner edge portions 24 are then removed from backing 10 and the corresponding portions of adhesive coated backing 10 are pressed to the skin. Liner edge portions 24 are most easily removed by folding backing 10 along the end of edge portions 24 and, in one sliding motion, rolling adhesive coated backing 10 into position while simultaneously removing liner edge portion 24. As shown, liner edge portions 24 extend beyond backing 10 for ease in handling.

Figure 5:
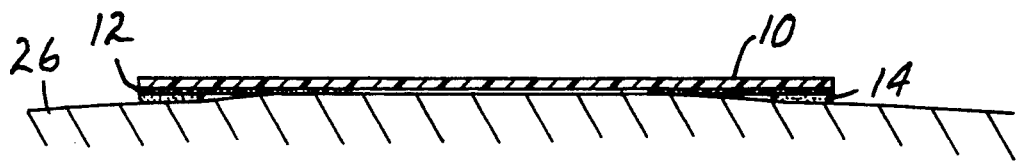
FIG. 5 is a cross-sectional view of a film dressing of FIG. 4 with the liner removed.

FIG. 5 shows the cross-sectional view of the adhesive composite of FIG. 4 after the liner portions have been removed, with the composite applied to surface 26.

DETAILED DESCRIPTION

The adhesive composite configuration of the present invention is useful in connection with any conformable backing having a pressure-sensitive adhesive coated onto it. Representative backings include non-woven fibrous webs, woven fibrous webs, knits, and other familiar backing materials. The preferred backing materials are polymeric films. The invention is particularly useful in pressure-sensitive adhesive composites having high moisture vapor permeable films. U.S. Pat. Nos. 3,645,835, and 4,595,001 describe methods of making such high vapor/moisture permeable films and methods for testing their permeability. The film/adhesive composite should transmit moisture vapor at a rate of at least 300 g/m²/24 hrs/37° C./100-10% RH. Preferably the adhesive coated film transmits moisture vapor at a rate of at least 700 g/m²/24 hrs/37° C./100-10% RH.

The backing and permanent adhesive reinforcement are preferably conformable to anatomical surfaces. This means that when the composite is applied to an animal anatomical surface it conforms to the surface even when the surface is moved. The preferred backings are also conformable to animal anatomical joints. When the joint is flexed and then returned to its unflexed position, the backing stretches to accommodate the flexion of the joint but is resilient enough to continue to conform to the joint when the joint is returned to its unflexed condition.

A measure of conformability is the "F" value which provides a measure of force necessary to extend a dressing. $F_{10}$ value as referred to herein is effectively determined using ASTM test method D 3759, except that the force measurements are taken at ten percent elongation. An Intelect II unit from Thwing-Albert Instrument Company (Philadelphia,, Pa.) is used in this test procedure to obtain these values. The cross-head speed of the Intelect II is set at ten inches per minute and the chart speed is set at ten inches (25.4 cm) per minute. The gauge length is set at two inches (5.1 cm) with the test sample cut to test a one-inch width (2.54 cm).

The $F_{10}$ value gives an approximation of the motion of the body surface and ability of a material to stretch with these body deformations. The $F_{10}$ value for the backing should be no greater than about 1 pound (454 grams) and preferably less than about 0.8 pounds (363 grams). In the preferred embodiments of wound dressings and drapes, backings which have $F_{10}$ values upwards of 2.5 pounds (1135 grams) may be used. However, as the $F_{10}$ value increases, the conformability decreases and the ability of the backing to perform comfortably as medical dressings likewise decreases.

Conformability is also somewhat dependent on thickness, thus the thinner the backing the more conformable it is. Generally, the films are from 12 to 25 microns thick. Examples of polymers which are suitable for use as wound dressing films in the present invention include polyurethane such as Estane, TM (B. F. Goodrich, Cleveland, Ohio), elastomeric polyester such as duPont Hytrel TM polyester elastomer (Wilmington, Del.), polyethylene, blends of polyurethane and polyester, chlorinated polyethylene, styrene/butadiene block copolymers such as Kraton TM brand thermoplastic rubber (Shell Chemical Company, Houston, Tex.), Pebox TM polyether block amides (distributed by Rilsan Corp., Glen Rock, N.J.), and polyvinyl chloride.

Particularly preferred backings are elastomeric polyurethane or polyester films. These films combine the desirable properties of resiliency, high moisture vapor permeability and transparency.

The preferred pressure-sensitive adhesives which can be used for both the backing adhesive and the permanent adhesive reinforcement in the preferred wound dressing embodiment are the normal adhesives which are applied to the skin such as the acrylate copolymers described in U.S. Pat. No. 24,906, particularly a 97:3 iso-octyl acrylate:acrylamide copolymer. Other useful adhesives are those described in U.S. Pat. No. 3,389,827, which discloses block copolymers having three or more polymer block structures having a general configuration -A-B-A-wherein each A block is a thermoplastic polymer with a glass transition temperature above room temperature (i.e., above about 20° C.) having an average molecular weight between about 5000 and 125,000 and the B block is a polymer of a conjugated diene having an average molecular weight between about 15,000 and 250,000. Additional examples of useful adhesives are iso-octyl acrylate/n-vinyl pyrrolidone copolymer adhesives and crosslinked acrylate adhesives such as, for example, those described in U.S. Pat. No. 4,112,213. Inclusion of medicaments or antimicrobial agents such as iodine in the adhesive is useful for enhancing wound healing and preventing infection. U.S. Pat. Nos. 4,310,509 and 4,323,557 describe such antimicrobial adhesives. As described below, the pressure-sensitive adhesive to be used in the permanent adhesive reinforcement is preferably higher tack than the selected backing adhesive.

Examples of liners suitable for use in the present invention are liners made of kraft papers, polyethylene, polypropylene, polyester or composites of any of these materials. These liners are coated with release agents such as fluorochemicals or silicone. U.S. Pat. No. 4,472,480 describes low surface energy perfluorochemical liners. The preferred liners are papers, polyolefin films, or polyester films coated with silicone release materials. Examples of the silicone coated release papers are Polyslik TM silicone release papers supplied by James River Co., H. P. Smith Division (Bedford Park, Ill.), and silicone coated papers supplied by Daubert Chemical Co.(Dixon, Ill.). The preferred liner is 1-60BKG-157 paper available from Daubert, which is a super calandered kraft paper with a water based silicone surface.

Other combinations of adhesives and liners are feasible. Those skilled in the art are familiar with processes of testing a new adhesive against different liners or a new liner against different adhesives in order to arrive at the combination of qualities desired in the final product. Handbook of Pressure-Sensitive Adhesive Technology, Chapter 18 "Silicone Release Coatings" Van Nostrand-Reinhold, 1982, pp. 384-403 describes the considerations pertinent to selection of a silicone release liner. U.S. Pat. No. 4,472,480 describes considerations pertinent to selection of a perfluoropolyether release liner. In the preferred wound dressing embodiment of the present invention, the choice of adhesive is limited to those that are safe to use on skin, and preferably to those that are of the class known as hypoallergenic. The preferred acrylate copolymers are adhesives of this class. Liners are available from a variety of manufacturers in a wide variety of proprietary formulations. One normally tests these in simulated use conditions against an adhesive of choice to arrive at a product with the desired release characteristics.

The permanent adhesive reinforcement is selected from adhesives or adhesive laminates which provide some reinforcing properties to the backing material. This permanent adhesive reinforcement may be a film-/adhesive laminate, such as Hytrel TM (duPont, Wilmington, Del.) film and tackified acrylate adhesive such as a copolymer of iso-octyl acrylate, acrylic acid and Foral 85 TM (a triglyceryl ester of reduced abietic acid, commercially available from Hercules Chemical Co., Wilmington, Del.) tackifier. Another permanent adhesive reinforcement may be a fabric/adhesive laminate. Examples of nonwoven fabric/adhesive laminates include embodiments such as disclosed in U.S. Pat. No. 4,366,814 and available commercially as Steri-Strip," (3M, St. Paul, Minn.) elastic skin closure, a nonwoven elastomeric melt blown web of thermoplastic elastomeric small diameter fibers, or Cerex ™ (Monsanto, St. Louis, Miss.) spun bonded nylon and adhesive. Woven fabric/adhesive laminates, include embodiments such as cotton cloth laminated to a rubber based adhesive.

As mentioned above, one of the embodiments of the nonwoven fabric/adhesive laminates for use as the permanent adhesive reinforcement is based on melt blown webs of thermoplastic elastomeric small diameter fibers, or blown microfiber (BMF) webs. Elastomeric thermoplastic materials from which the microfiber webs can be prepared include, for example, elastomeric polyurethanes, elastomeric polyesters, elastomeric polyamides and elastomeric A-B-A' block copolymers wherein A and A' are styrenic moieties and B is an elastomeric midblock.

Elastic properties of the nonwoven webs are controlled by the size of the fiber making up the web and the basis weight of the web. The elastomeric small diameter fibers preferably have diameters of from about 1 micron to about 50 microns and are more preferably from about 5 microns to about 30 microns. When the diameter of the small diameter fibers is less than 1 micron, the web may lack sufficient tensile strength. When the diameter of the small diameter fibers is greater than about 50 microns, the contact surface area for adhesive anchorage decreases.

The basis weight of the nonwoven elastomeric web is also a major factor in controlling the elastic properties of the web. Web basis weights are preferably in the range of from about 15 to 150 grams/m$^2$ and are more preferably in the range of from about 20 to about 70 gm/m$^2$.

The nonwoven elastomeric web when used as a permanent adhesive reinforcement preferably has a machine direction tensile strength of at least about 30 g/2.5 cm width/g/m$^2$ basis weight and more preferably at least about 40 g/2.5 cm width/g/m$^2$ basis weight. After being stretched 50% in the machine direction, the nonwoven elastomeric web preferably recovers at least about 85%, more preferably at least about 90%, most preferably at least about 95%. After being stretched 50% in the cross direction, the web preferably recovers at least about 80%, more preferably at least about 85% and most preferably at least about 90%.

An example of an elastomeric, nonwoven, melt blown microfiber web suitable for use in a permanent adhesive reinforcement is prepared using thermoplastic elastomeric polyurethane polymer (PS 440-101 or 200, a polyesterurethane available from K. J. Quinn Co., Malden, Mass.) and a process similar to that described in Wente, Van A., "Superfine Thermoplastic Fibers" in Industrial Engineering Chemistry, Vol. 48, pages 1342 et seq (1965), or in Report No. 4364 of the Naval Research Laboratories, published May 25, 1964 entitled "Manufacture of Superfine Organic Fibers" by Wente, Van A., Boone, C. D. and Fluharty, E. L. except that the melt-blowing die has smooth surfaced orifices (10/cm) with a 5:1 length-to-diameter ratio and a drilled die is preferably used. The thermoplastic elastomeric materials are extruded through the die into a high velocity stream of heated air which draws out and attenuates the fibers prior to their solidification and collection. The fibers are collected in a random fashion, such as on a perforated screen cylinder, prior to complete fiber solidification so that the fibers are able to bond to one another and form a coherent web which does not require additional binders. In forming the permanent adhesive reinforcement of the invention, the blown fibers can be collected directly on an adhesive film carried on a release liner. Specific physical characteristics of the web are achieved by properly balancing the polymer rheology, the fiber forming and collection phases of the process to achieve desired web properties. The die temperature is maintained at 220° C., the primary air temperature and pressure are, respectively, 230° C. and 150 kPa, (0.63 mm gap width), and the polymer throughput rate is 450 gm/hr/cm. The resulting web has a fiber size of 5-10 microns and a basis weight of 60 g/m$^2$.

A variety of pressure-sensitive adhesives can be used with the nonwoven web of the permanent adhesive reinforcement, but acrylate-based pressure-sensitive adhesives are preferred because of their hypoallergenicity and gas permeability and particularly preferred are acrylate-based medical pressure-sensitive adhesives because of their skin adhesion properties. The pressure-sensitive adhesive can be applied on the nonwoven elastomeric microfiber web as a solution or a latex or, alternatively, the elastomeric web can be laminated to an adhesive film or collected directly on an adhesive film. The amount of adhesive applied on the web is preferably in the range of from about 30 to 60 weight percent of the web basis weight, more preferably from about 35 to about 50 percent of the web basis weight.

An alternative embodiment of a permanent adhesive reinforcement may be a thicker amount of any adhesive which is conventional in the pressure-sensitive adhesive composite art, supplied in an amount which gives sufficient rigidity to the backing material that it does not readily fold back on itself or wrinkle under ordinary use. This additional "bead" of adhesive is located on the backing in any pattern which provides structural support to the backing while it is being applied by the user. The additional adhesive may alternatively contain fibers for additional structural reinforcement, such as the fiber filled transfer adhesive described in U.S. Pat. No. 3,062,683.

Regardless of the particular permanent adhesive reinforcement which is selected for use, the permanent adhesive reinforcement is provided in an amount which gives sufficient rigidity to the backing material that it does not readily fold back on itself or wrinkle under ordinary use. Although the permanent adhesive reinforcement may be located on the backing in any pattern which provides support or increases handleability, the preferred application is to the periphery of the backing to provide a frame or border which is coterminous with the backing. Another preferred pattern is the application of two parallel strips of permanent adhesive reinforcement material to the border region of the two opposing edges of the backing that bridge the edges held by the user during application of the backing to the surface.

The amount of permanent adhesive reinforcement material required depends on the relative flimsiness of the backing, the size of the total composite, and the reinforcing properties of the permanent adhesive reinforcement. For example, the permanent adhesive reinforcement may provide reinforcing properties through the bulk of the adhesive material present or through orientation of fibers in the adhesive or through the substrate material in an adhesive laminate. Depending on the properties of the permanent adhesive reinforcement, the width of the permanent adhesive reinforcement border may be narrower on smaller dressings and wider on larger dressings.

An additional feature which the permanent adhesive reinforcement provides is a stretchable reinforcement border. As described above, an important application of the composites of this invention is as medical dressings. The amount of conformability and stretchability provided by the permanent adhesive reinforcement should be less than the film itself, in order to provide additionally rigidity, but more than a frame made of paper or other stiff material, so that the dressing will not pop off upon ordinary movement of the anatomical substrate.

The adhesive composite of this invention provides a very low profile dressing. The permanent adhesive reinforcement need be provided only in a reinforcing amount to inhibit wrinkling. Thus, the permanent adhesive reinforcement need generally be no thicker than about 500 microns, preferably no thicker than about 250 microns and most preferably no thicker than about 125 microns.

Optimally, the permanent adhesive reinforcement of this invention provides a better edge seal to a surface through the use of a higher tack adhesive in the permanent adhesive reinforcement. An adhesion to skin of the permanent adhesive reinforcement which is more than about 1.25 times the adhesion to skin of the backing adhesive as determined by panel studies provides good edge seal. Most preferably, the permanent adhesive reinforcement has an adhesion to skin which is more than about 1.50 times the adhesion to skin of the backing adhesive. The use of higher tack adhesives in the permanent adhesive reinforcement allows for the use of lower amounts of (or lower coating weights of) backing adhesive, which can provide a greater vapor permeability of the dressing in the portion of the dressing in direct contact with the wound.

The composite of the present invention may be made by conventional techniques (e.g., extrusion, solvent casting, calendering, and laminating and the like) which are familiar to those skilled in the art. (See Modern Plastics Encyclopedia McGraw Hill, 1984-85; Coating and Laminating Machines, Weiss Coverting Technology Co., 1977.) The method of making a composite is further exemplified by the following non-limiting examples.

EXAMPLE 1

Twenty-five grams per square meter of an adhesive prepared in accordance with U.S. Pat. No. 24,906, comprising a 97:3 units of iso-octyl acrylate: acrylamide copolymer was applied to a release liner of 78 pounds per ream (127 grams per meter squared) bleached, one-side coated, polyethlylene and silicone paper (Polyslik S-8053, James River Co., H. P. Smith Division, Bedford Park, Ill.) utilizing a standard horizontal knife coater. A 1.1 mil (28 micron) film of "Estane 58309NAT022" polyurethane resin (B. F. Goodrich, Cleveland, Ohio) was laminated to the adhesive surface. The center portion of a backing/adhesive laminate prepared in accordance with U.S. Pat. No. 4,366,814 and commercially available from 3 M Company as Steri-Strip TM Elastic, was removed and the peripheral frame portion laminated to the above structure after removal of the S-8053 release liner to form the permanent adhesive reinforcement frame. The adhesive used on the frame was higher tack than the center of the dressing. The exposed adhesive was then relaminated to a release liner of 60 pound per ream (97.6 grams per meter squared) bleached super calandered kraft paper, coated on both sides with silicone (2-60BKG-157/99AM, Daubert, Chicago, Ill.). This liner was die cut into three parts. The framed laminate was then cut to size.

Dressings were made in accordance with this example in a small size having overall dimensions of 6 cm $\times$ 7 cm and having a frame of permanent adhesive reinforcement of 64 mm width. Larger size dressings were made having overall dimensions of 10 cm $\times$ 12cm and having a frame of permanent adhesive reinforcement of 127 mm width.

EXAMPLE 2

Dressings of both sizes described above were prepared per Example 1, except the permanent adhesive reinforcement frame consisted of a nonwoven polyurethane web prepared from 60 grams per square meter basis weight microfibrous polyurethane resin #P.S. 440 from K. J. Quinn. This backing is coated with twenty-five grams per square meter of an adhesive having 56.4 parts iso-octyl acrylate, 3.6 parts acrylic acid and 40 parts Foral 85 TM tackifier, available from Hercules Chemical Co., Wilmington, Del.

EXAMPLE 3

Dressings of both sizes described above were prepared per Example 1, except the permanent adhesive frame consisted of a fibrous adhesive mix laminated to the edge of the backing at the rate of fifty grams per square meter of backing. This fiberous adhesive mix was prepared as taught in U.S. Pat. No. 3,062,683, and consisted of 99% of a mixture containing 56.4 parts iso-octyl acrylate, 3.6 parts acrylic acid, 40 parts Foral 85 TM, and 1% of blended Polyester Staple Fiber, 1.5 Denier, 0.250 inches long (Type 790 Semi-Dull) commercially available from Minifibers, Inc., Johnson City, Tenn.

EXAMPLE 4

Dressings of both sizes described above were prepared per Example 1, except the permanent adhesive frame consisted of a film/adhesive laminate. The film was 1.1 mil Hytrel TM 4056, commercially available from DuPont. The adhesive was prepared in accordance with U.S. Pat. No. 4,323,557 and consisted of iso-octyl acrylate/n-vinyl pyrrolidone together with 2% iodine salt and 2% iodide crystals. This adhesive was applied at a rate of 50 grams per square meter.

Handleability Studies

The adhesive composite, as described above, is easier to handle than like composites without a permanent adhesive reinforcement while continuing to be conformable as shown by the measurements of thickness, $F_{10}$ modulus and Handle-O-Meter data. The method of measuring the $F_{10}$ modulus and significance of this data has been discussed above. The "Handle-O-Meter" data measures conformability of materials by measuring effects of forces perpendicular to the material. This measurement is made in accordance with a modified INDA Standard Test for Handle-O-Meter stiffness, IST 90.0-75 (R82) or TAPPI T498 Su-66. This test was modified in that 2.5 cm by 7.6 cm samples were measured and actual readings were taken from a 200 gram scale. The adhesive coated surfaces of the samples were coated with talc powder and were placed in the instrument adhesive side up. Readings were taken in grams-force units and were taken in both the machine and cross directions.

Table 1 sets forth measurements of these data, comparing a thin film dressing (Tegaderm TM 1626) alone and with a coating of the indicated permanent adhesive reinforcement material to a total sample thickness as indicated.

TABLE 1

| Adhesive/<br>Film | Thickness<br>(microns) | $F_{10}$ Value<br>(grams-force)<br>(machine/cross) | Handle-O-Meter<br>(grams-force)<br>(machine/cross) |
|---|---|---|---|
| Tegaderm TM 1626* | 48 | 104/100 | .43/.47 |
| Fiber filled (Example #3) | 112 | 350/95 | 2.50/1.53 |
| Steri-Strip TM Elastic (Example #1) | 244 | 7209/608 | 35.80/13.17 |
| elastomeric BMF Example #2) | 170 | 286/150 | 9.63/4.53 |
| IOBAN TM 2 iodophor (Example #4) | 127 | 499/545 | 1.97/1.60 |

*commercially available from 3M Company

Skin Adhesion Test

As noted above, the permanent adhesive reinforcement optimally provides a better edge seal of the composite to a surface through use of a higher tack adhesive as compared to the backing adhesive. A quantitative measurement of adhesive tack to skin is provided by the test method which follows.

The adhesive-coated sheet material to be tested is cut into 1×3 inch (2.5×7.6 cm) strips which are applied to the (dry) backs of each of 6 individuals (i.e., 3 men and 3 women, randomly selected) who are lying on procedure tables in prone positions with arms at the sides and heads turned to one side. For each individual, each of three strips of the sheet material is applied to one or the other side of the spinal column and is positioned such that the length of the strip is at right angles to the spinal column. The strips are applied without tension or pulling of the skin and there is at least a 32 to 95 mm space between each strip. After all strips are in place, a 20.4 kg rubber roller according to the specifications found in the 7th Edition of the Pressure-Sensitive Tape Council Brochure (1976), incorporated herein by reference, is rolled along the length of each strip. When rolling the strip, no manual pressure should be applied to the roller.

To determine the adhesive value, each strip is removed at a 90° angle from a line formed by the spinal column using a conventional adhesion tester having a 114 kg test line and a 2.54 cm clip attached to the test line. The clip is attached to the edge of the strip which is farthest from the spinal cord, the clip being attached by manually lifting about 1.27 cm of that edge of the strip and attaching the clip thereto. This orientation permits the strip to be removed starting from the outside of the back towards the spine so that pull is with the direction of fine hair growth on the back. This is facilitated by positioning the adhesion tester opposite the side of the individual's back from which the strip is to be removed. The adhesion tester is aligned with and is at the same height as the strip to be removed in order to maintain the 90° removal angle. The strip is pulled over itself in a plane parallel (180°) to the back and the rate of removal is 6 inches (15.2 cm) per minute. To determine initial skin adhesion, the strip is removed within about 5 minutes of its application to the back.

An example of a suitable adhesion tester for use in this Test Method comprises a conventional motor driven screw with moving carriage and a transducer. Connected to the transducer is a load cell accessory. Removal force placed on the transducer results in a signal change which is passed through a readout meter to a strip chart recorder.

A preferred permanent adhesive reinforcement material in accordance with the invention exhibits an average initial dry skin adhesion value of at least about 2 Newtons per 100 millimeters of width.

Comparative adhesion to skin measurements of the dressing of Example 4 were measured at the time of initial application to the skin (T-O) and forty-eight hours later (T-48). The results of this test are set forth in Table 2 below.

TABLE 2

| | Adhesion To Skin (N/100 mm) | | Material Desc. |
|---|---|---|---|
| | T-0 | T-48 | |
| Frame | 3.55 | 15.87 | Hytrel with IOA/NVP/Iodine Adh. |
| Center | 1.70 | 5.98 | Polyurethane with IOA/Acrylamide |

The foregoing description has been directed to particular preferred embodiments for purposes of illustration and explanation. Those skilled in the art will appreciate that many modifications will be possible without departing from the spirit of the invention. For example, the composite may further comprise an absorbent pad or adhesive voids to increase moisture vapor transmission.

I claim:

1. An adhesive composite comprising:
    a) a conformable backing having top and bottom faces;
    b) a backing adhesive that is a pressure-sensitive adhesive coated on at least a portion of the bottom face of the backing;
    c) a reinforcing amount of a permanent adhesive reinforcement that is an adhesive or adhesive laminate applied to the bottom face of the backing and that is inseparable from the backing; and
    d) a liner releasably adhered to he exposed adhesive on the backing.

2. The composite according to claim 1 wherein the backing adhesive is located between the backing and the permanent adhesive reinforcement so that the permanent adhesive reinforcement is exposed after removal of the liner and will adhere directly to the surface after application.

3. The composite according to claim 1 wherein the permanent adhesive reinforcement is applied to the periphery of the backing.

4. The composite according to claim 1 wherein said backing has two opposing end edges held by a user during application of the backing to the surface and two opposing side edges that bridge the end edges, wherein the permanent adhesive reinforcement is applied to a border region of the two opposing side edges.

5. The composite according to claim 1 wherein the permanent adhesive reinforcement is a laminate consisting of a layer of a film material and a layer of adhesive.

6. The composite according to claim 1 wherein the permanent adhesive reinforcement is a laminate consisting of a layer of fabric material and a layer of adhesive.

7. The composite according to claim 6 wherein the fabric is a nonwoven web.

8. The composite according to claim 6 wherein the fabric is woven.

9. The composite according to claim 1 wherein the permanent adhesive reinforcement is a fiber filled adhesive.

10. The composite according to claim 1 having delivery means comprising two parallel die cuts in the liner forming a central portion and two side portions that may be removed independently of each other.

11. The composite according to claim 1 having delivery means comprising the attachment of optionally removable tabs to opposing edges of the top face of the backing.

12. The composite according to claim 1 wherein the permanent adhesive reinforcement is less than about 500 microns thick.

13. The composite according to claim 1 wherein the permanent adhesive reinforcement is less than about 250 microns thick.

14. The composite according to claim 1 wherein the permanent adhesive reinforcement is less than about 125 microns thick.

15. The composite according to claim 2 wherein the permanent adhesive reinforcement possesses an adhesion to skin which is more than about 1.25 times the adhesion to skin of the backing adhesive.

16. The composite according to claim 2 wherein the permanent adhesive reinforcement possesses an adhesion to skin which is more than about 1.50 times the adhesion to skin of the backing adhesive.

17. The composite according to claim 1 wherein the backing, backing adhesive and permanent adhesive reinforcement together have an $F_{10}$ value of less than about 7300 grams force in any direction.

18. The composite according to claim 1 wherein the backing, backing adhesive and permanent adhesive reinforcement together have an $F_{10}$ value of less than about 600 grams in any direction.

19. The composite according to claim 1 wherein the backing, backing adhesive and permanent adhesive reinforcement together have a Handle-O-Meter reading of no less than about 1 gram-force.

20. The composite according to claim 1 wherein the backing consists of polyurethane or polyester.

21. The composite according to claim 1 wherein the composite is a dressing that transmits moisture vapor at a rate of at least 300 g/m$^2$/24 hrs/37° C./100–10% RH.

22. The composite according to claim 20 wherein the backing is transparent.

23. The composite according to claim 1 wherein the backing has an $F_{10}$ value of no greater than about 454 grams force.

* * * * *

UNITED STATES PATENT AND TRADEMARK OFFICE
CERTIFICATE OF CORRECTION

PATENT NO. : 5,088,483
DATED : February 18, 1992
INVENTOR(S) : Steven B. Heinecke It is certified that error appears in the above-identified patent and that said Letters Patent is hereby corrected as shown below:

Abstract, line 13, "wall" should be --will--.

Col. 4, line 7, "out" should be --cut--.

Col. 5, lines 50/51, "Pebox™" should be --Pebax™--.

Col. 12, line 46, "he" should be --the--.

Signed and Sealed this

Thirteenth Day of July, 1993

Attest:

MICHAEL K. KIRK

Attesting Officer

Acting Commissioner of Patents and Trademarks